US006539947B2

(12) United States Patent
Boies et al.

(10) Patent No.: US 6,539,947 B2
(45) Date of Patent: Apr. 1, 2003

(54) APPARATUS, SYSTEM, METHOD AND COMPUTER PROGRAM PRODUCT FOR CONTROLLING BIO-ENHANCEMENT IMPLANTS

(75) Inventors: Stephen J. Boies, Mahopac, NY (US); Sam Dinkin, Austin, TX (US); David P. Greene, Ossining, NY (US); William Grey, Millwood, NY (US); Paul A. Moskowitz, Yorktown Heights, NY (US); Philip S. Yu, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/736,469

(22) Filed: Dec. 12, 2000

(65) Prior Publication Data

US 2002/0069885 A1 Jun. 13, 2002

(51) Int. Cl.⁷ .......................... A61B 19/00; A61B 5/04; A61N 1/18
(52) U.S. Cl. ...................... 128/899; 600/510; 607/9
(58) Field of Search ............... 607/27, 32, 30, 607/9, 55–57, 60, 25; 600/558, 485, 510, 521; 128/899

(56) References Cited

U.S. PATENT DOCUMENTS

| | | | | |
|---|---|---|---|---|
| 5,291,399 A | | 3/1994 | Chaco | 364/413.02 |
| 5,324,315 A | * | 6/1994 | Grevious | 607/60 |
| 5,752,976 A | * | 5/1998 | Duffin et al. | 607/32 |
| 5,792,204 A | * | 8/1998 | Snell | 607/32 |
| 5,836,989 A | * | 11/1998 | Shelton | 607/27 |
| 6,032,155 A | | 2/2000 | de la Huerga | 707/104 |
| 6,056,734 A | | 5/2000 | Jacobsen et al. | 604/891.1 |
| 6,092,530 A | | 7/2000 | Weissman et al. | 128/899 |
| 6,170,488 B1 | * | 1/2001 | Spillman, Jr. et al. | 128/899 |
| 6,223,072 B1 | * | 4/2001 | Mika et al. | 600/510 |
| 6,120,460 A1 | * | 9/2001 | Abreu | 600/558 |

* cited by examiner

*Primary Examiner*—Eric F. Winakur
*Assistant Examiner*—Nikita R Veniaminov
(74) *Attorney, Agent, or Firm*—Duke W. Yee; Stephen J. Walder, Jr.; Stephen C. Kaufman (57) ABSTRACT

An apparatus, system, method and computer program product for monitoring and controlling bio-enhancement implants is provided. With the apparatus, system, method and computer program product, a user may control the operation of implantable devices within the user's body by operation of a personal digital device. The personal digital device may obtain operational settings of the various implantable devices based on information stored within the personal digital device and/or information obtained from a network. The settings of the various implants are established in view of the possible interactions of the implants with one another. The personal digital device further monitors the operation of the implantable devices and the user's biological indicia. Based on the monitoring, the operation of the implantable devices are modified to obtain a desired result. If an emergency situation is encountered, the personal digital device may contact emergency response services with the location of the user so that emergency personnel are dispatched accordingly.

58 Claims, 6 Drawing Sheets

APPARATUS, SYSTEM, METHOD AND COMPUTER PROGRAM PRODUCT FOR CONTROLLING BIO-ENHANCEMENT IMPLANTS

BACKGROUND OF THE INVENTION

1. Technical Field

The present invention provides an apparatus, system, method and computer program product for controlling bio-enhancement implants. In particular, the present invention provides a mechanism by which a user may control the operation of bio-enhancement implants to provide a desired result.

2. Description of Related Art

The field of medical science is a rapidly evolving one. Advancements in medical science seem to be made at an ever increasing rate. For example, recently a pace maker, having a size smaller than a quarter, was implanted into a premature newborn and was successfully used to regulate the newborn's heart beat. Other amazing medical devices have been recently devised and introduced to our communities.

For example, U.S. Pat. No. 6,056,734 to Jacobsen et al., entitled "Method for Automatic Dosing of Drugs," describes an implantable device having doses of drugs. A timer of the implantable device may be remotely triggered by a transmitter outside the body of the organism in which the implantable device is implanted.

U.S. Pat. No. 6,092,530 to Weissman et al., entitled "Remotely Interrogated Implant Device with Sensor for Detecting Accretion of Biological Matter" describes an implant device which has a sensor for detection the accretion of biological material. The sensor is operatively coupled to a communication element which communicates wirelessly to a remotely located element outside the organism in which the implant device is implanted.

Enhancement of individual's characteristics through surgical means is being increasingly accepted by society. Cosmetic surgery, surgery to combat obesity, sex change operations, and many other "elective" procedures are more common place today than ever before and are becoming more accepted by mainstream society.

As medical implants become more advanced, individuals will increasingly elect to have these implants surgically implanted into their bodies in a similar manner that cosmetic surgery is now becoming common place. It is conceivable that individuals may have many different implants that may interfere or otherwise interact with one another. Thus, it would be beneficial to have an apparatus, system, method and computer program product for controlling these implants, in view of their interactions with one another, to obtain results desired by the user.

SUMMARY OF THE INVENTION

The present invention provides an apparatus, system, method and computer program product for monitoring and controlling bio-enhancement implants. With the present invention, a user may control the operation of implantable devices within the user's body by operation of a personal digital device. The personal digital device may obtain operational settings of the various implantable devices based on information stored within the personal digital device and/or information obtained from a network. The settings of the various implants are established in view of the possible interactions of the implants with one another.

The personal digital device further monitors the operation of the implantable devices and the user's biological indicia. Based on the monitoring, the operation of the implantable devices are modified to obtain a desired result. If an emergency situation is encountered, the personal digital device may contact emergency response services with the location of the user so that emergency personnel are dispatched accordingly. Other features and advantages of the present invention will be described in, or will become apparent to those of ordinary skill in the art in view of, the following detailed description of the preferred embodiments.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE PREFERRED EMBODIMENTS

Figure 1:
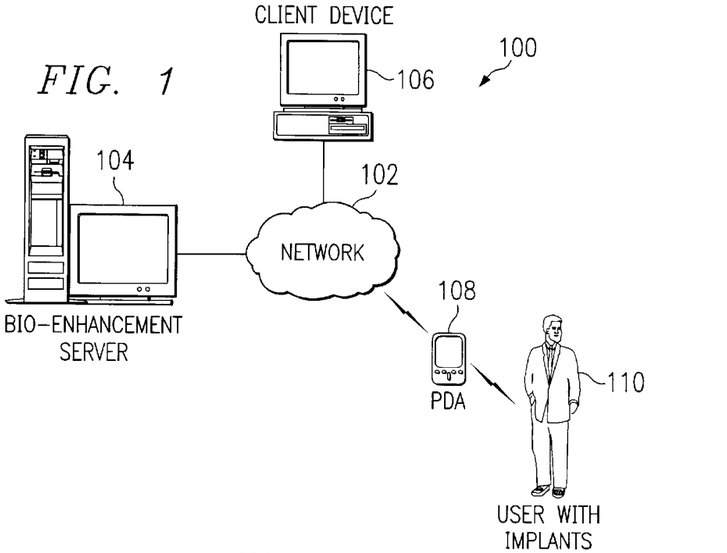
FIG. 1 is an exemplary block diagram of a distributed data processing system in accordance with the present invention.

With reference now to the figures, FIG. 1 depicts a pictorial representation of a network of data processing systems in which the present invention may be implemented. Network data processing system 100 is a network of computers in which the present invention may be implemented. Network data processing system 100 contains a network 102, which is the medium used to provide communications links between various devices and computers connected together within network data processing system 100. Network 102 may include connections, such as wire, wireless communication links, or fiber optic cables.

In the depicted example, a bio-enhancement server 104 is connected to network 102. In addition, client devices 106–108 are also connected to network 102. The client devices 106–108 may be, for example, personal computers, portable computers, personal digital assistants, wearable computers, network computers, or the like. The bio-enhancement server 104 provides data and applications to client devices 106–108. Client devices 106–108 are clients to server 104. Network data processing system 100 may include additional servers, clients, and other devices not shown.

In the depicted example, network data processing system 100 is the Internet with network 102 representing a worldwide collection of networks and gateways that use the TCP/IP suite of protocols to communicate with one another. At the heart of the Internet is a backbone of high-speed data communication lines between major nodes or host computers, consisting of thousands of commercial, government, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the present invention.

With the present invention, an individual, such as the individual 110, is surgically altered to include one or more bio-enhancement implants. Such implants may include pace makers, muscle stimulant devices, drug dosing devices, such as that described in U.S. Pat. No. 6,056,734, which is hereby incorporated by reference, monitoring devices, such as that described in U.S. Pat. No. 6,092,530, which is also hereby incorporated by reference, or the like. Various implantable devices may be used without departing from the spirit and scope of the present invention. The implants are preferably equipped with transceivers for transmitting and receiving information with the client device 108.

The bio-enhancement server 104 compiles various information regarding individuals 110, such as their individual bio-enhancement implants, their medical information, various activities performed by the individuals and the settings of their implants during those activities, and the like. The information may be obtained, for example, from the client devices 106–108, from the individuals themselves, or obtained from some other source. For example, the client device 108 may monitor the activities of the individual 110, the settings and operation of his/her implants, and report this information back to the bio-enhancement server 104 via a wireless communication link and network 102.

The client device 108 is a personal digital device that is preferably portable or wearable by the user. In a preferred embodiment, the client device 108 is a personal digital assistant (PDA), such as a Palm Pilot™, Nino™, or the like. The client devices 106–108 may include a software application for entering information regarding the user's biological implants, the activities that are to be performed by the user, and downloading implant setting information from the bio-enhancement server 104 via the network 102.

The software application is provided with information about the individual configuration of the user's biological implants. The configuration information may be input by the user or, in the case of the client device 108, may be obtained from interrogating the biological implants themselves using a wireless communication link and broadcasting a request for configuration information to the biological implants.

The user, via the client device 108 or client device 106, inputs a desired activity and parameters about the activity. For example, the user may enter into the client device 106 the parameters regarding a mountain hike that the user plans on attempting. Such parameters may include the starting and ending elevations, the length of the hike, the time that the hike should take, the weather conditions, the user's weight, or any other type of parameter information that may be pertinent for determining the proper operation of the implants and the user's body.

Based on the activity parameter information and the user's implant configuration information, the client device 106 or 108, sends a request for recommended implant settings to the bio-enhancement server 104. Alternatively, the implant settings may be determined based on information stored completely within the client device 108 using an application that takes the activity parameter information and implant configuration information as input and generates settings based on this information. One benefit from using a bio-enhancement server 104 is that information uploaded to the bio-enhancement server 104 may be used to refine the bio-enhancement server's optimized settings based on actual experiences of users.

The settings determined by either the bio-enhancement server 104 or the client device 108 may be settings that are recommended to provide a certain result. In a preferred embodiment, the settings are "optimal" settings determined using an application or algorithm that optimizes the settings of the various implants taking into consideration the cross effects of the implant operations with each other. The present invention, however, is not limited to determining "optimal" settings and non-optimal settings may be determined and/or recommended by the bio-enhancement server 104 or client device 108 without departing from the spirit and scope of the present invention. For purposes of the following description, it will be assumed that optimal settings are determined for the implants.

Whether performed entirely within the client device 108, or with the aid of the bio-enhancement server 104, a software application generates optimized implant settings based on the activity parameter information and the implant configuration information. The optimized settings may indicate, for example, the setting of the implant as well as the expected result obtained from the biological system directly affected by the implant.

The software application takes into consideration the possible interactions of the various implants identified in the implant configuration information. For example, the software application may adjust settings of a heart implant from a first setting to a second setting based on the fact that the implant configuration information indicates that the user also has a respiratory system implant. In this way, an overall optimization of all of the user's implants with respect to one another, is obtained based on the particular activity that the user wishes to engage in.

The client device 106 may be used to enter activity and implant configuration information and obtain optimized implant operational settings. The optimized implant operational settings may then be downloaded to the client device 108 via a wired or wireless connection between the client devices 106 and 108. The client device 108 may then store the optimized implant operational settings until the user is ready to make use of them.

Once the optimized operational settings of the implants are determined and stored in the client device 108, the user may implement the optimized settings at any time. Thus, the user may, for example, input a command to transmit the optimized implant operational settings to the user's implants when the user starts the desired activity. The client device 108 then transmits the optimized implant operational settings to the user's implants via a wireless connection.

The user's implants contain wireless transceivers for receiving and sending messages and data from and to the client device 108. The user's implants receive the optimized setting information from the client device 108 via the wireless transceivers and adjust their operation accordingly.

Periodically, the implants will report back to the client device 108, actual measured operation information of the implant and any biological systems directly affected by the implant. For example, if the implant is a heart implant that affects the beats-per-minute of the user's heart, the implant will periodically report back to the client device 108 the actual period of impulses applied by the heart implant and the beats-per-minute being obtained through use of the implant.

The client device 108 receives the monitored operational information and compares it to the optimized settings and the expected biological system results. Based on this comparison, the client device 108 determines a new adjustment of the implant to obtain a desired result from the biological system. In this way, the implants provide information to the client device 108 and the implant operation is adjusted using a feedback loop. Of course, this feedback loop adjustment also takes into consideration the latest information obtained from the other user implants in a manner similar to the determination of the optimized settings.

In addition to using the feedback information obtained from the implants to adjust their operation, the feedback information may further be used to determine if an emergency situation is presently occurring or there is a threat of an emergency situation occurring. The determination of an actual or potential emergency situation may be performed based on threshold information stored in the client device 108.

If reported information of a biological system indicates that the biological system is operating within an emergency range as determined by established thresholds, the client device 108 will indicate an emergency situation is either occurring or dangerously close to occurring. If an emergency situation is identified, the client device 108 may send a command to the implants to cease functioning, if this is in the best interest of the user's health, or to function in such a manner as to best preserve the user's health. In addition, the client device 108 may be equipped with a location determination device, such a global positioning system (GPS), for identifying the location of the user. The location of the user may then be sent to an emergency response service using the wireless transceiver of the client device 108 so that emergency personnel may be dispatched to the user's location. For example, the client device 108 may call contact a 911 emergency response communication line and transmit the location of the user so that an ambulance or paramedic unit may be dispatched.

Once the user has completed the desired activity, the user may discontinue use of the implants by inputting a command to discontinue into the client device 108. When the command to discontinue is received, the client device 108 transmits a command to the implants to discontinue operation. In response the implants may discontinue operation. Such discontinuing of the operation of the implants may require a slow or gradual ramping down of the operation so that irreparable harm is not caused to the user's biological systems.

In addition to discontinuing the operation of the implants, the client device 108 may send a history report to the bio-enhancement server 104 via a wireless communication connection to the network 102. The history report may include, for example, the optimum settings for the implants, the actual operation of the implants and the corresponding biological systems, and the like. This information may be stored in the bio-enhancement server 104 in conjunction with a user identifier, for example. The information may be used in future implant usage to obtain a refined optimization of the implant settings. The history report information may be used only with the user or with a plurality of users registered with the bio-enhancement server to better refine the determination of optimum implant settings for various activities.

Thus, the present invention provides a mechanism by which one or a plurality of implants may be monitored and controlled to obtain optimum performance of the user's biological systems. The present invention allows for determination of optimum settings of implants based on previously compiled implant setting information by other users involved in similar activities. In addition, the present invention provides the ability to notify emergency services should the user's biological systems be placed into an emergency situation.

Figure 2:
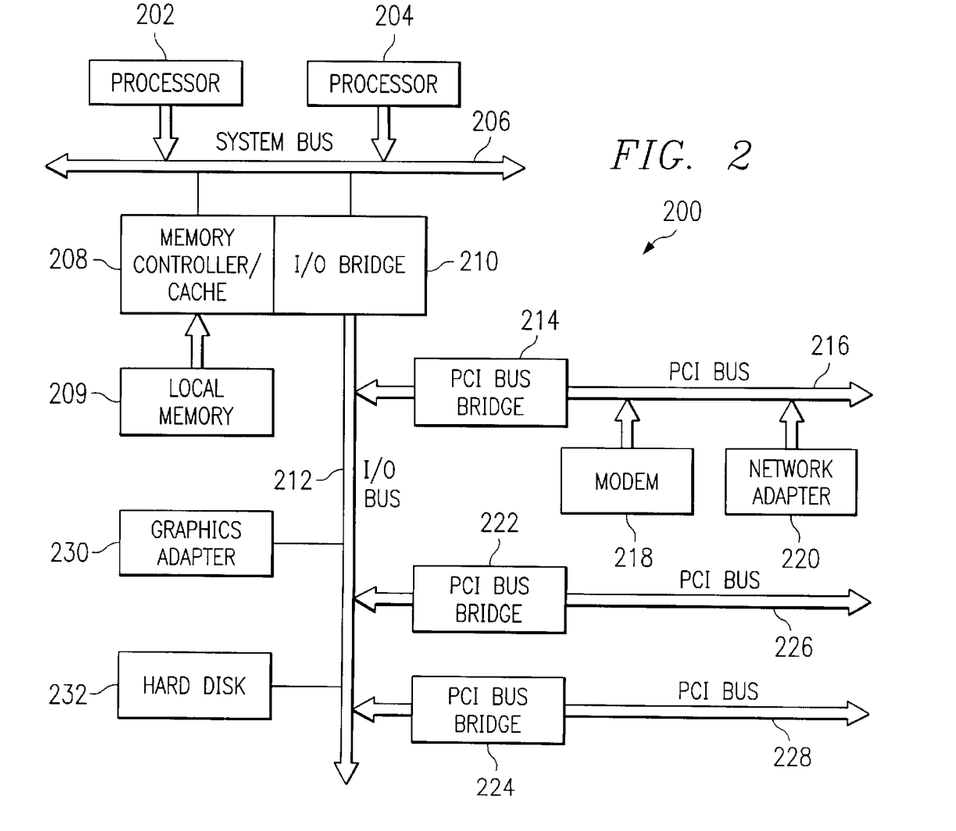
FIG. 2 is an exemplary block diagram of a data processing system that may be used to implement the server of the present invention.

Referring to FIG. 2, a block diagram of a data processing system that may be implemented as a server, such as server 104 in FIG. 1, is depicted in accordance with a preferred embodiment of the present invention. Data processing system 200 may be a symmetric multiprocessor (SMP) system including a plurality of processors 202 and 204 connected to system bus 206. Alternatively, a single processor system may be employed. Also connected to system bus 206 is memory controller/cache 208, which provides an interface to local memory 209. I/O bus bridge 210 is connected to system bus 206 and provides an interface to I/O bus 212. Memory controller/cache 208 and I/O bus bridge 210 may be integrated as depicted.

Peripheral component interconnect (PCI) bus bridge 214 connected to I/O bus 212 provides an interface to PCI local bus 216. A number of modems may be connected to PCI bus 216. Typical PCI bus implementations will support four PCI expansion slots or add-in connectors. Communications links to network computers 108–112 in FIG. 1 may be provided through modem 218 and network adapter 220 connected to PCI local bus 216 through add-in boards.

Additional PCI bus bridges 222 and 224 provide interfaces for additional PCI buses 226 and 228, from which additional modems or network adapters may be supported. In this manner, data processing system 200 allows connections to multiple network computers. A memory-mapped graphics adapter 230 and hard disk 232 may also be connected to I/O bus 212 as depicted, either directly or indirectly.

Those of ordinary skill in the art will appreciate that the hardware depicted in FIG. 2 may vary. For example, other peripheral devices, such as optical disk drives and the like, also may be used in addition to or in place of the hardware depicted. The depicted example is not meant to imply architectural limitations with respect to the present invention.

The data processing system depicted in FIG. 2 may be, for example, an IBM RISC/System 6000 system, a product of International Business Machines Corporation in Armonk, N.Y., running the Advanced Interactive Executive (AIX) operating system.

Figure 3:
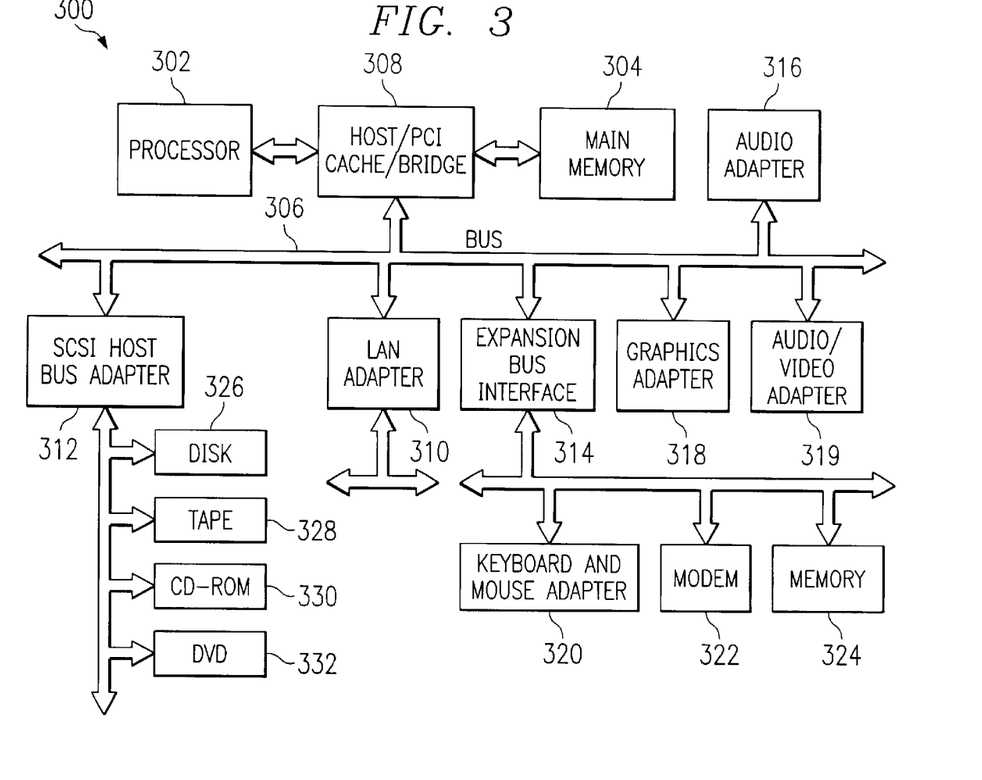
FIG. 3 is an exemplary block diagram of a data processing system that may be used to implement a client system in accordance with the present invention.

With reference now to FIG. 3, a block diagram illustrating a data processing system is depicted in which the present invention may be implemented. Data processing system 300 is an example of a client computer. Data processing system 300 employs a peripheral component interconnect (PCI) local bus architecture. Although the depicted example employs a PCI bus, other bus architectures such as Accelerated Graphics Port (AGP) and Industry Standard Architecture (ISA) may be used.

Processor 302 and main memory 304 are connected to PCI local bus 306 through PCI bridge 308. PCI bridge 308 also may include an integrated memory controller and cache memory for processor 302. Additional connections to PCI local bus 306 may be made through direct component interconnection or through add-in boards. In the depicted example, local area network (LAN) adapter 310, SCSI host bus adapter 312, and expansion bus interface 314 are connected to PCI local bus 306 by direct component connection. In contrast, audio adapter 316, graphics adapter 318, and audio/video adapter 319 are connected to PCI local bus 306 by add-in boards inserted into expansion slots.

Expansion bus interface 314 provides a connection for a keyboard and mouse adapter 320, modem 322, and additional memory 324. Small computer system interface (SCSI) host bus adapter 312 provides a connection for hard disk drive 326, tape drive 328, and CD-ROM drive 330. Typical PCI local bus implementations will support three or four PCI expansion slots or add-in connectors.

An operating system runs on processor 302 and is used to coordinate and provide control of various components within data processing system 300 in FIG. 3. The operating system may be a commercially available operating system, such as Linux or Windows 2000, which is available from Microsoft Corporation. An object oriented programming system such as Java may run in conjunction with the operating system and provide calls to the operating system from Java programs or applications executing on data processing system 300. "Java" is a trademark of Sun Microsystems, Inc. Instructions for the operating system, the object-oriented operating system, and applications or programs are located on storage devices, such as hard disk drive 326, and may be loaded into main memory 304 for execution by processor 302.

Those of ordinary skill in the art will appreciate that the hardware in FIG. 3 may vary depending on the implementation. Other internal hardware or peripheral devices, such as flash ROM (or equivalent nonvolatile memory) or optical disk drives and the like, may be used in addition to or in place of the hardware depicted in FIG. 3. Also, the processes of the present invention may be applied to a multiprocessor data processing system.

As another example, data processing system 300 may be a stand-alone system configured to be bootable without relying on some type of network communication interface, whether or not data processing system 300 comprises some type of network communication interface. As a further example, data processing system 300 may be a Personal Digital Assistant (PDA) device, which is configured with ROM and/or flash ROM in order to provide nonvolatile memory for storing operating system files and/or user-generated data.

The depicted example in FIG. 3 and above-described examples are not meant to imply architectural limitations. For example, data processing system 300 also may be a notebook computer or hand held computer in addition to taking the form of a PDA. Data processing system 300 also may be a kiosk or a Web appliance.

Figure 4:
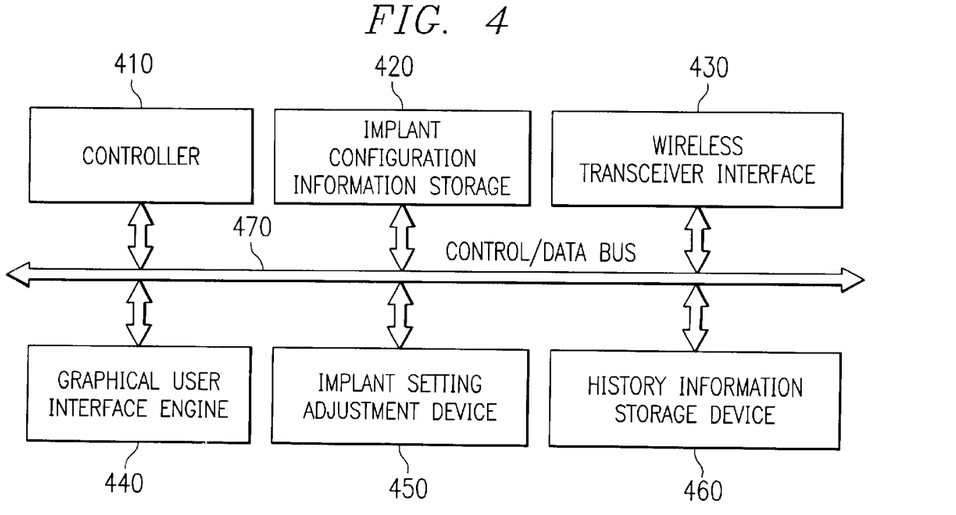
FIG. 4 is an exemplary block diagram of a personal digital device according to the present invention.

FIG. 4 is an exemplary block diagram illustrating a personal digital device, such as client device 108, according to the present invention. As shown in FIG. 4, the personal digital device includes a controller 410, an implant configuration information storage device 420, a wireless transceiver interface 430, a graphical user interface engine 440, an implant setting adjustment device 450, and a history information storage device 460. The elements 410–460 are in communication with one another via control/data bus 470. Although a bus architecture is shown in FIG. 4, any architecture may be used which facilitates the exchange of control messages and data among the elements 410–460 without departing from the spirit and scope of the present invention.

The elements 410–460 may be implemented as hardware devices, software instructions, or a combination of hardware devices and software instructions. For example, the elements 410–460 may be implemented as software instructions executed by processor 302 and hardware devices depicted in FIG. 3.

The controller 410 controls the overall operation of the personal digital device. The controller 410 instructs the other elements 420–460 in their operation, coordinates operations among the various elements 420–460 and performs other functions as necessary. The controller 410 further receives messages and data via the wireless transceiver interface 430 and routes the messages and data to the appropriate elements 420–460.

The implant configuration information storage device 420 stores implant configuration information for the user of the personal digital device. The implant configuration information may be obtained from inputs by the user, through interrogating implants in the user, or the like. The implant configuration information is then used to determine optimized implant settings for various activities as well as adjusting the implant settings to obtain a desired biological system operation, as described above.

The wireless transceiver interface 430 is used to send and receive messages and data to devices outside the personal digital device. The wireless transceiver interface 430 is used to communicate information to the bio-enhancement server 104 via the network 102, to the implants within the body of the user, to the client device 106, and the like.

The graphical user interface engine 440 is used to generate graphical user interfaces on the personal digital device in order to provide the user with information and receive inputs from the user. The graphical user interface engine 440 generates interfaces having virtual buttons that may be operated by way of a pointing device, touch screen, stylus and touch screen, or the like. Through the graphical user interfaces, the user may enter desired activity parameter information, implant configuration information, requests for optimized implant settings, commands to start and/or stop implant optimization, commands to contact emergency services, and the like.

The implant setting adjustment device 450 receives information regarding the implant configuration of the user from the implant configuration information storage device 420, actual implant and biological system operating conditions from the wireless transceiver interface 430 and/or history information storage device 460, and the like. Based on this information, the implant setting adjustment device 450 may adjust the settings of the various implants to obtain a desired biological system result. In an embodiment in which optimized implant settings are determined within the personal digital device, the implant setting adjustment device 450 may determine these optimized implant settings.

The history information storage device 460 stores history information regarding the optimum settings of the various implants of the user, the actual implant and biological system operations occurring, and the like. The history information storage device 460 may provide this information to the implant setting adjustment device 450 and/or the bio-enhancement server 104 for use in adjusting the settings of the user's implants to obtain a desired biological system operating result. This history information may further be used by the bio-enhancement server 104 to refine the determination of optimum implant settings for other registered users of the bio-enhancement server 104.

Figure 5:
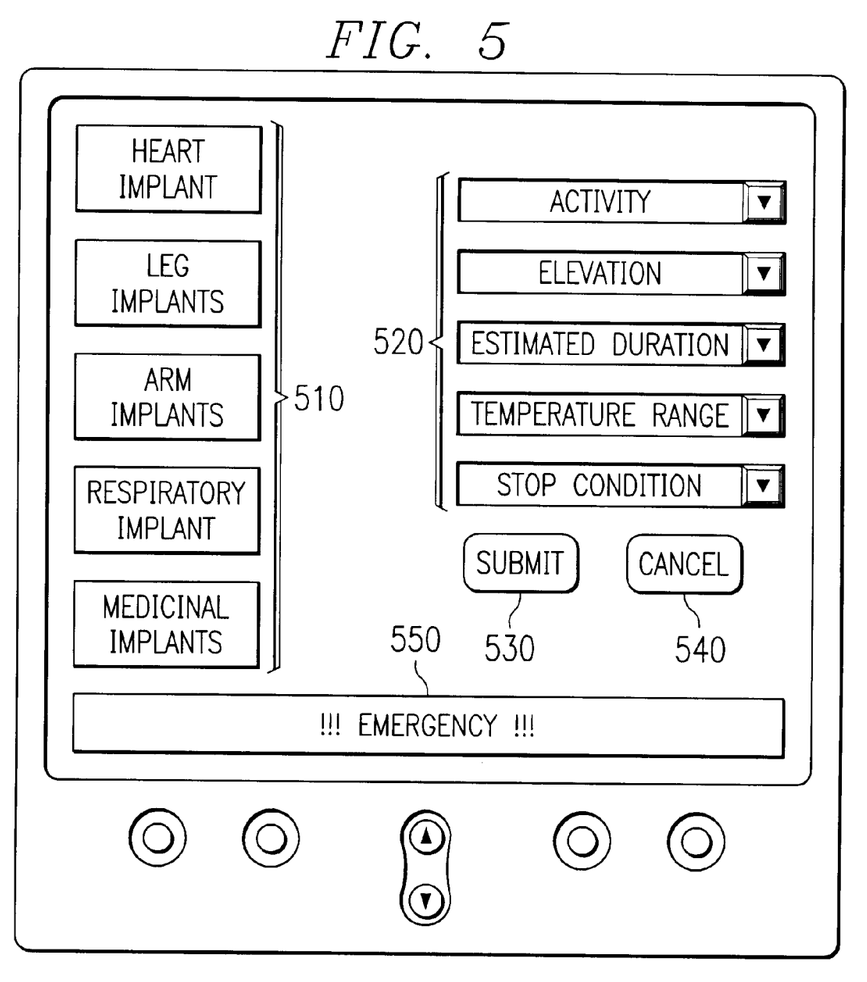
FIG. 5 is an exemplary diagram illustrating a graphical user interface for setting parameters for bio-enhancement implants in accordance with the present invention.

FIG. 5 is an exemplary block diagram illustrating a graphical user interface for entering information regarding the desired activity of the user. As shown in FIG. 5, the graphical user interface includes one or more virtual buttons 510 for accessing information regarding various implants of the user. The particular implant buttons shown to the user will depend on the implants determined to be within the user's body based on information entered by the user, an interrogation of implants, or the like. Through the virtual buttons 510, the user may obtain information relating the types of each implant, the current operational status, and the like.

A plurality of pull down menus 520, or other input receiving devices, are provided for entering activity parameters regarding the activity for which the user desires bio-enhancement implants to be activated. The activity parameters may be any parameters that may affect the operation of the bio-enhancement implants including the particular activity, elevation, estimated duration of the activity, ambient temperature of the location in which the activity will take place, any stop condition that the user may wish for stopping the operation of the implants, and the like.

The graphical user interface further includes a virtual button 530 for submitting the activity parameters for use in determining optimum settings for the various implants. Another virtual button 540 is provided for canceling the user's selection of activity parameters. Still another virtual button 550 is provided for the user to indicate that an emergency situation has occurred and requesting that the personal digital device contact emergency services personnel.

Figure 6:
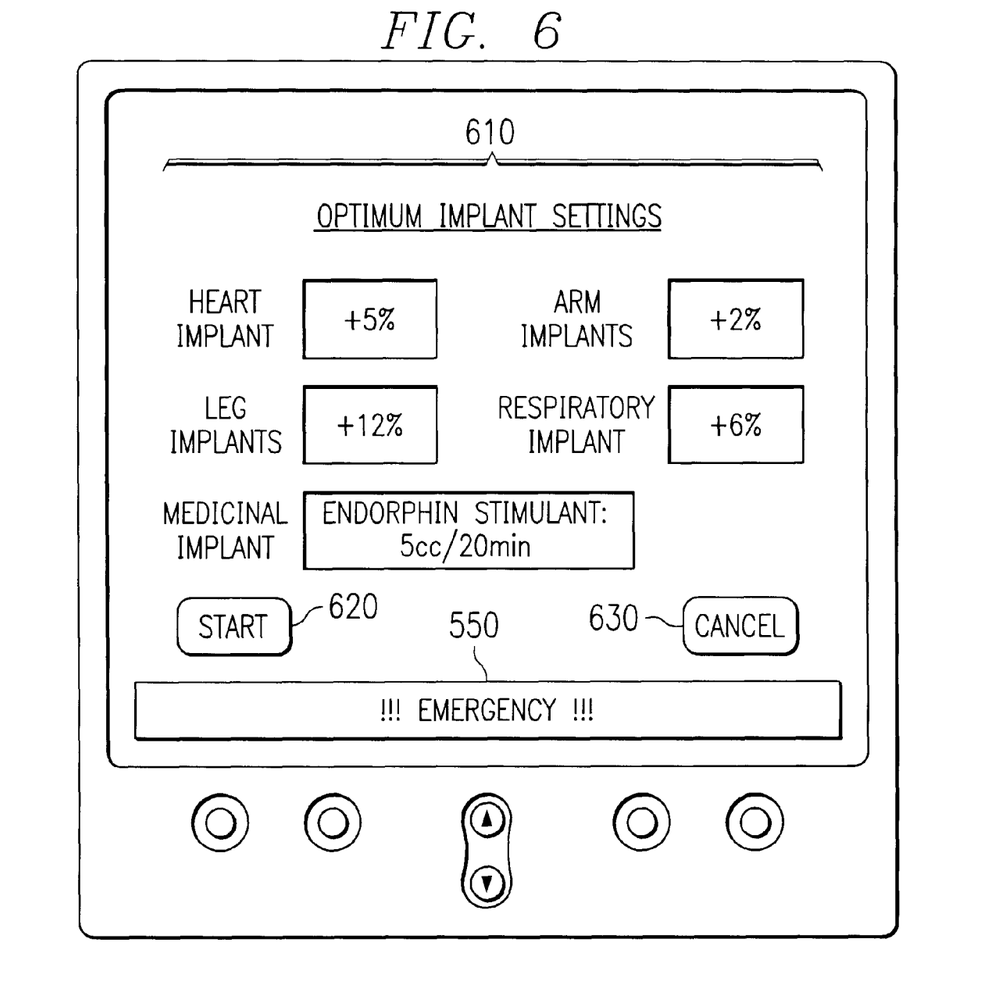
FIG. 6 is an exemplary diagram illustrating a graphical user interface for starting operation of bio-enhancement implants based on received settings, in accordance with the present invention.

FIG. 6 is an exemplary block diagram illustrating a graphical user interface for displaying optimum implant settings and initiating the use of optimum implant settings in accordance with the present invention. As shown in FIG. 6, the graphical user interface includes one or more fields for identifying the optimum implant settings in accordance with the optimum implant settings determined by either the personal digital device or the bio-enhancement server 104. The graphical user interface further includes a virtual button 620 for initiating use of the optimum implant settings, a virtual button 630 for canceling the use of the optimum implant settings, and an emergency virtual button 550. When the virtual button 620 is selected by the user, the optimum implant settings are sent to the implants which then use these settings to adjust their operation. The sending of the optimum implant settings may further include the gradual increase of the operation of the implants from a standard condition to the optimum settings in order to avoid and possible damage to the user's biological systems.

Figure 7:
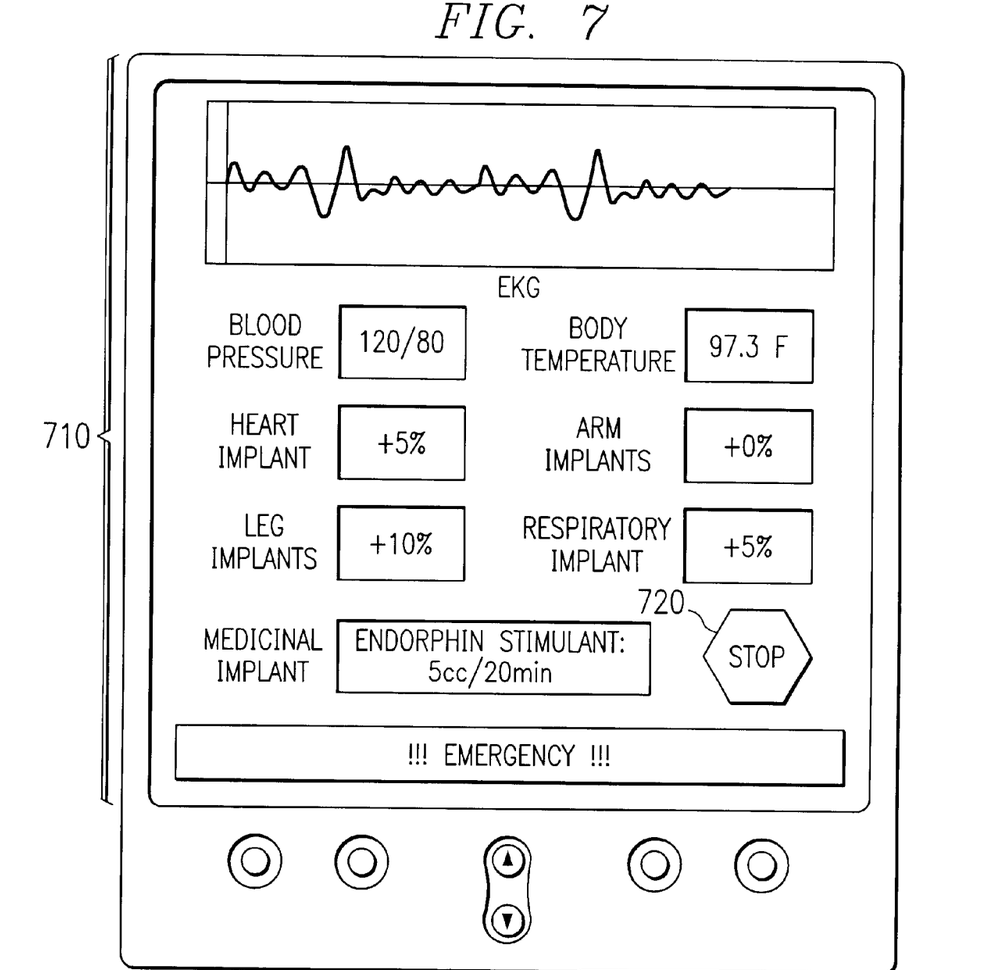
FIG. 7 is an exemplary diagram illustrating a graphical user interface for monitoring the operation of bio-enhancement implants in accordance with the present invention.

FIG. 7 is an exemplary block diagram illustrating a graphical user interface for displaying current implant and biological system operating conditions. As shown in FIG. 7, the graphical user interface includes one or more fields 710 for informing the user of current implant and biological system conditions. In addition, the graphical user interface includes a virtual button 720 for stopping the operation of the implants. The fields 710 are updated periodically based on measured results obtained from the implants. When the virtual button 720 is selected by the user, the implants are returned to a standard setting. The return of the implants to a standard setting may be performed immediately or gradually in order to avoid damage to the user's biological systems.

Figures 8, 9:
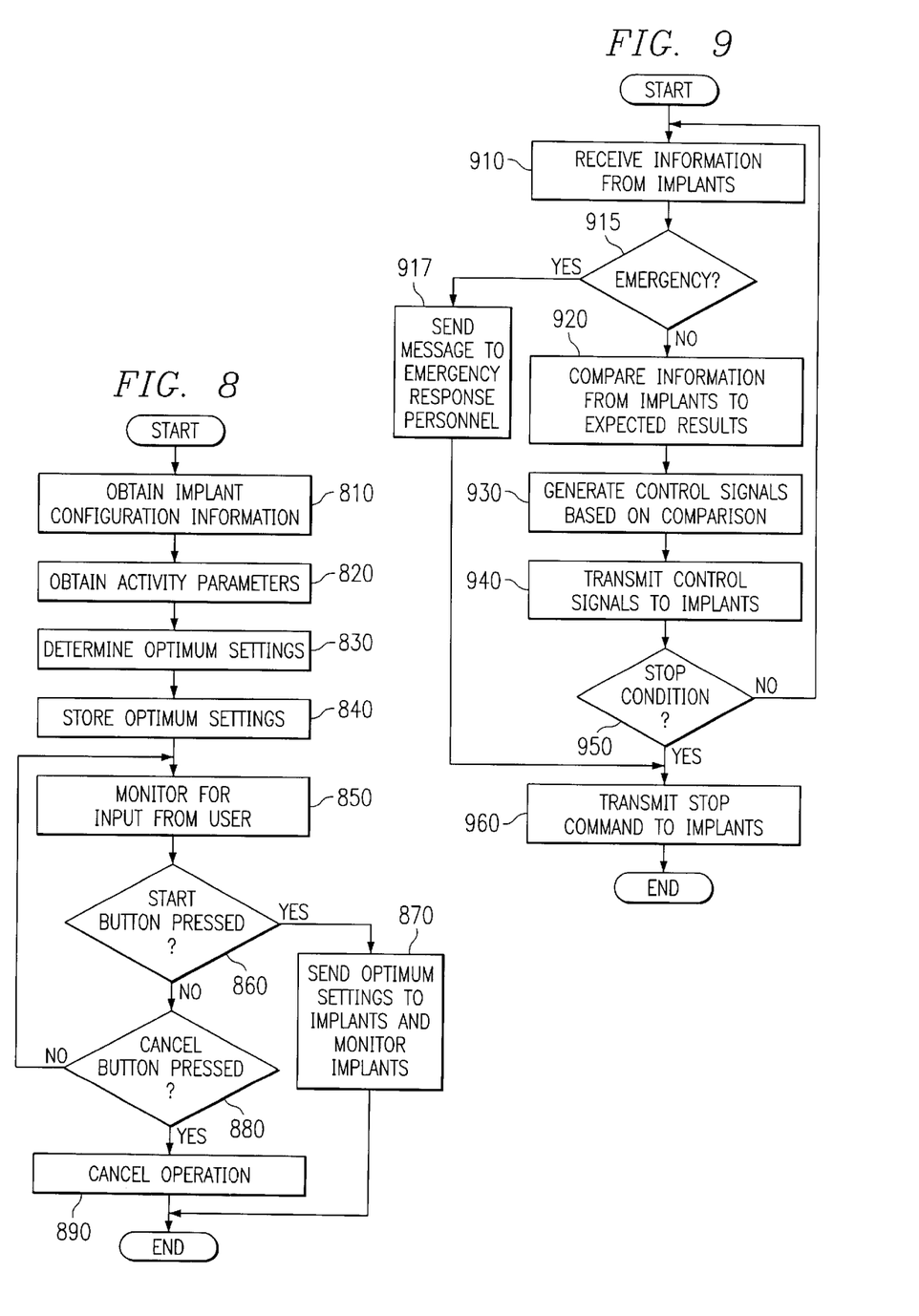
FIG. 8 is a flowchart outlining an exemplary operation of the present invention when determining optimum operating settings for the bio-enhancement implants.
FIG. 9 is a flowchart outlining an exemplary operation of the present invention when monitoring the operation of bio-enhancement implants.

FIG. 8 is a flowchart outlining an exemplary operation of the present invention when determining optimum operating settings for the bio-enhancement implants. As shown in FIG. 8, the operation starts with obtaining implant configuration information (step 810). Thereafter, activity parameter information is obtained (step 820). The optimum implant settings are then determined based on the implant configuration information and the activity parameter information (step 830). The optimum implant settings are stored in the personal digital device (step 840) and the input interface is monitored for selection of the start virtual button to start use of the optimum settings (step 850).

A determination is then made as to whether or not the start virtual button is selected (step 860). If the start virtual button is selected, the optimum settings are sent to the implants and the implant operation is monitored (step 870). If the start virtual button is not selected, a determination is made as to whether a cancel button is selected (step 880). If so, the operation is canceled (step 890) and the operation ends. If the cancel button is not selected, the operation returns to step 850 where monitoring for input from the user is continued.

FIG. 9 is a flowchart outlining an exemplary operation of the present invention when monitoring the operation of bio-enhancement implants. The operation starts with receiving information from the implants regarding their current operation and the operation of the biological systems associated with the implants (step 910). A determination is made as to whether or not an emergency situation has occurred (step 915). If so, a message is sent to emergency response personnel identifying the user's current location (step 917). If not, the operation continues to step 920.

The information from the implants is compared to expected operation information (step 920). Control signals are generated based on the difference between the expected operation information and the measured information obtained from the implants (step 930). The control signals are then transmitted to the implants (step 940).

A determination is made as to whether or not a stop condition has occurred (step 950). A stop condition may be, for example, the input of a stop command by the user, or the like. If a stop condition has not occurred, the operation returns to step 910 and continues to monitor and adjust the operation of the implants. If the stop condition occurs, a stop command is sent to the implants (step 960) and the operation ends.

Thus, the present invention provides a mechanism by which a user may monitor and control the operation of one or more bio-enhancement implants in the user's body. Furthermore, the present invention may make use of historical information for identifying the optimum settings for the implants taking into consideration the possible interaction of the implants with one another. In addition, the present invention provides a mechanism by which, if an emergency situation arises, the emergency response personnel may be notified of the user's location for immediate dispatch of emergency personnel to aid the user.

It is important to note that while the present invention has been described in the context of a fully functioning data processing system, those of ordinary skill in the art will appreciate that the processes of the present invention are capable of being distributed in the form of a computer readable medium of instructions in a variety of forms and that the present invention applies equally regardless of the particular type of signal bearing media actually used to carry out the distribution. Examples of computer readable media include recordable-type media such a floppy disk, a hard disk drive, a RAM, a CD-ROM, and transmission-type media such as digital and analog communications links.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A method for controlling one or more implantable devices, comprising:
    obtaining activity information identifying a physical activity to be performed by a user of the one or more implantable devices;
    obtaining configuration information for the one or more implantable devices; and
    determining a setting for the one or more implantable devices based on the activity information and the configuration information.

2. The method of claim 1, wherein the activity information includes at least one of an indicator of the activity, starting elevation, ending elevation, length of the activity, a user's weight, ambient temperature, and period of time of the activity.

3. The method of claim 1, wherein the configuration information is obtained from inputs received from a user.

4. The method of claim 1, wherein the configuration information is obtained from interrogating the one or more implantable devices.

5. The method of claim 1, wherein determining the setting for the one or more implantable devices includes taking into consideration possible interactions of implantable devices identified in the configuration information.

6. The method of claim 1, wherein determining the setting for the one or more implantable devices includes:
    sending the activity information and the configuration information to a server; and
    receiving the setting for the one or more implantable devices from the server.

7. The method of claim 6, wherein the server determines the setting for the one or more implantable devices based on the activity information, the configuration information and history information compiled from one or more registered users of the server.

8. The method of claim 7, wherein the history information compiled from one or more registered users of the server includes information identifying settings of implantable devices associated with the one or more registered users.

9. The method of claim 1, further comprising transmitting the setting for the one or more implantable devices to the one or more implantable devices.

10. The method of claim 9, further comprising:
    monitoring an operation of the one or more implantable devices; and
    controlling the operation of the one or more implantable devices to obtain a desired operation.

11. The method of claim 9, wherein controlling the operation of the one or more implantable devices includes:
    obtaining operation information from the one or more implantable devices; and
    sending commands to the one or more implantable devices based on a comparison of the operation information to the desired operation.

12. The method of claim 1, further comprising:
    monitoring an operation of a biological system of a user of the one or more implantable devices;
    determining if the operation of the biological system indicates an emergency situation; and
    notifying emergency personnel of a location of the user if the operation of the biological system indicates an emergency situation.

13. The method of claim 12, wherein notifying emergency personnel of a location of the user includes obtaining a location of the user from a global positioning device.

14. The method of claim 10, wherein determining if the operation of the biological system indicates an emergency situation includes:
    comparing measured operational parameters of the biological system to a threshold; and
    determining if an emergency situation is present based on the comparison.

15. The method of claim 1, further comprising activating use of the setting by the one or more implantable devices.

16. The method of claim 15, further comprising:
    deactivating use of the setting by the one or more implantable devices; and
    uploading a history report of an operation of the one or more implantable devices and an operation of a corresponding biological system to a server.

17. The method of claim 1, wherein the method is implemented in a personal digital device.

18. The method of claim 17, wherein the personal digital device is one of a personal digital assistant, a notebook computer, a hand held computer, a Web appliance, a cellular telephone, and a wearable computer.

19. The method of claim 1, wherein the method is implemented in a client-server distributed data processing system.

20. The method of claim 1, wherein the setting is an optimal setting.

21. The method of claim 1, wherein the method is implemented in one of a personal digital assistant, a handheld computer, a cellular telephone, and a wearable computer.

22. An apparatus for controlling one or more implantable devices, comprising:
    a first interface for obtaining activity information identifying a physical activity to be performed by a user of the one or more implantable devices;
    a second interface for obtaining configuration information for the one or more implantable devices; and
    a computing device for determining a setting for the one or more implantable devices based on the activity information and the configuration information.

23. The apparatus of claim 22, wherein the activity information includes at least one of an indicator of the activity, starting elevation, ending elevation, length of the activity, a user's weight, ambient temperature, and period of time of the activity.

24. The apparatus of claim 22, wherein the second interface is an input interface through which the configuration information is obtained from inputs received from a user.

25. The apparatus of claim 22, wherein the second interface is a transceiver through which configuration information is obtained from interrogating the one or more implantable devices.

26. The apparatus of claim 22, wherein the computing device determines the setting for the one or more implantable devices taking into consideration possible interactions of implantable devices identified in the configuration information.

27. The apparatus of claim 22, further comprising a transceiver, wherein the computing device is a server and wherein the activity information and the configuration information is transmitted to the server.

28. The apparatus of claim 27, wherein the server determines the setting for the one or more implantable devices based on the activity information, the configuration information and history information compiled from one or more registered users of the server.

29. The apparatus of claim 22, further comprising a transmitter for transmitting the setting for the one or more implantable devices to the one or more implantable devices.

30. The apparatus of claim 29, further comprising:
a monitoring device for monitoring an operation of the one or more implantable devices; and
a controller for controlling the operation of the one or more implantable devices to obtain a desired operation.

31. The apparatus of claim 30, wherein the controller includes a receiver for receiving operation information from the one or more implantable devices, wherein the controller transmits, via the transmitter, commands to the one or more implantable devices based on a comparison of the operation information to the desired operation.

32. The apparatus of claim 22, further comprising:
a monitor device for monitoring an operation of a biological system of a user of the one or more implantable devices;
means for determining if the operation of the biological system indicates an emergency situation; and
means for notifying emergency personnel of a location of the user if the operation of the biological system indicates an emergency situation.

33. The apparatus of claim 32, wherein the means for notifying emergency personnel of a location of the user includes a global positioning device for obtaining a location of the user.

34. The apparatus of claim 22, further comprising means for activating use of the setting by the one or more implantable devices.

35. The apparatus of claim 30, further comprising:
means for deactivating use of the setting by the one or more implantable devices; and
means for uploading a history report of an operation of the one or more implantable devices and an operation of a corresponding biological system to a server.

36. The apparatus of claim 22, wherein the apparatus is a personal digital device.

37. The apparatus of claim 36, wherein the personal digital device is one of a personal digital assistant, a notebook computer, a hand held computer, a Web appliance, a cellular telephone, and a wearable computer.

38. The apparatus of claim 22, wherein the apparatus is part of a client-server distributed data processing system.

39. The apparatus of claim 22, wherein the setting is an optimal setting.

40. A computer program product in a computer readable medium for controlling one or more implantable devices, comprising:
first instructions for obtaining activity information identifying a physical activity to be performed by a user of the one or more implantable devices;
second instructions for obtaining configuration information for the one or more implantable devices; and
third instructions for determining a setting for the one or more implantable devices based on the activity information and the configuration information.

41. The computer program product of claim 40, wherein the activity information includes at least one of an indicator of the activity, starting elevation, ending elevation, length of the activity, a user's weight, ambient temperature, and period of time of the activity.

42. The computer program product of claim 40, wherein the configuration information is obtained from inputs received from a user.

43. The computer program product of claim 40, wherein the configuration information is obtained from interrogating the one or more implantable devices.

44. The computer program product of claim 40, wherein the third instructions for determining the setting for the one or more implantable devices includes instructions for taking into consideration possible interactions of implantable devices identified in the configuration information.

45. The computer program product of claim 40, wherein the third instructions for determining the setting for the one or more implantable devices includes:
instructions for sending the activity information and the configuration information to a server; and
instructions for receiving the setting for the one or more implantable devices from the server.

46. The computer program product of claim 40, wherein the server determines the setting for the one or more implantable devices based on the activity information, the configuration information and history information compiled from one or more registered users of the server.

47. The computer program product of claim 40, further comprising fourth instructions for transmitting the setting for the one or more implantable devices to the one or more implantable devices.

48. The computer program product of claim 47, further comprising:
fifth instructions for monitoring an operation of the one or more implantable devices; and
sixth instructions for controlling the operation of the one or more implantable devices to obtain a desired operation.

49. The computer program product of claim 48, wherein controlling the operation of the one or more implantable devices includes:
seventh instructions for obtaining operation information from the one or more implantable devices; and
eighth instructions for sending commands to the one or more implantable devices based on a comparison of the operation information to the desired operation.

50. The computer program product of claim 40, further comprising:
fourth instructions for monitoring an operation of a biological system of a user of the one or more implantable devices;
fifth instructions for determining if the operation of the biological system indicates an emergency situation; and sixth instructions for notifying emergency personnel of a location of the user if the operation of the biological system indicates an emergency situation.

51. The computer program product of claim 50, wherein the sixth instructions for notifying emergency personnel of a location of the user includes instructions for obtaining a location of the user from a global positioning device.

52. The computer program product of claim 40, further comprising fourth instructions for activating use of the setting by the one or more implantable devices.

53. The computer program product of claim 52, further comprising:

fifth instructions for deactivating use of the setting by the one or more implantable devices; and sixth instructions for uploading a history report of an operation of the one or more implantable devices and an operation of a corresponding biological system to a server.

54. The computer program product of claim 40, wherein the computer program product is executed in a personal digital device.

55. The computer program product of claim 54, wherein the personal digital device is one of a personal digital assistant, a notebook computer, a hand held computer, a Web appliance, a cellular telephone, and a wearable computer.

56. The computer program product of claim 40, wherein the computer program product is executed in a client-server distributed data processing system.

57. The computer program product of claim 40, wherein the setting is an optimal setting.

58. A method of controlling the operation of a plurality of implantable devices implanted in a human user, comprising:

obtaining configuration information from the plurality of implantable devices; and determining a setting for a selected implantable device of the plurality of implantable devices taking into consideration possible interactions of the operation of the selected implantable device on the operation of the other implantable devices of the plurality of implantable devices.

* * * * *